US012144977B2

(12) United States Patent
Nitzan et al.

(10) Patent No.: US 12,144,977 B2
(45) Date of Patent: Nov. 19, 2024

(54) INTRAVASCULAR CATHETERS (71) Applicant: White Swell Medical Ltd, Kibbutz Shefayim (IL)

(72) Inventors: Yaacov Nitzan, Hertzelia (IL); Sagi Raz, Tel-Aviv (IL)

(73) Assignee: White Swell Medical Ltd, Kibbutz Shefayim (IL)

( * ) Notice: Subject to any disclaimer, the term of this patent is extended or adjusted under 35 U.S.C. 154(b) by 0 days.

(21) Appl. No.: 16/968,799

(22) PCT Filed: Feb. 12, 2019

(86) PCT No.: PCT/IB2019/000139
§ 371 (c)(1),
(2) Date: Aug. 10, 2020

(87) PCT Pub. No.: WO2019/158996
PCT Pub. Date: Aug. 22, 2019

(65) Prior Publication Data
US 2020/0397963 A1 Dec. 24, 2020

Related U.S. Application Data

(60) Provisional application No. 62/629,914, filed on Feb. 13, 2018.

(51) Int. Cl.
*A61M 60/13* (2021.01)
*A61M 60/135* (2021.01)
(Continued)

(52) U.S. Cl.
CPC .......... *A61M 60/829* (2021.01); *A61M 60/13* (2021.01); *A61M 60/135* (2021.01);
(Continued)

(58) Field of Classification Search
CPC .. A61M 60/205; A61M 60/414; A61M 60/40; A61M 1/0058; A61M 25/0662
See application file for complete search history.

(56) References Cited

U.S. PATENT DOCUMENTS 3,211,150 A 10/1965 Foderick
3,884,240 A 5/1975 Gilman
(Continued)

FOREIGN PATENT DOCUMENTS

EP 0526102 A1 2/1993
EP 2353501 A1 8/2011
(Continued)

OTHER PUBLICATIONS

Bannon, 2011, Anatomic considerations for central venous cannulation, Risk Manag Healthc Policy 4:27-39.
(Continued)

*Primary Examiner* — Michael J D'Abreu
(74) *Attorney, Agent, or Firm* — Brown Rudnick LLP; Adam M. Schoen (57) ABSTRACT

The disclosure provides an intravascular catheter with a purge system that excludes biological fluids and may also include devices such as impellers that can be delivered over, and operated over, a guidewire. Catheters may include treatment devices suited to the treatment of edema and in which the guidewire aids in positioning the device while the purge system facilitates reliable operation.

16 Claims, 9 Drawing Sheets

(51) Int. Cl.
*A61M 60/216* (2021.01)
*A61M 60/414* (2021.01)
*A61M 60/416* (2021.01)
*A61M 60/829* (2021.01)
*A61M 60/833* (2021.01)
*A61M 60/857* (2021.01)

(52) U.S. Cl.
CPC ........ *A61M 60/216* (2021.01); *A61M 60/414* (2021.01); *A61M 60/416* (2021.01); *A61M 60/833* (2021.01); *A61M 60/857* (2021.01)

(56) References Cited

U.S. PATENT DOCUMENTS

| | | | |
|---|---|---|---|
| 3,926,175 | A | 12/1975 | Allen et al. |
| 4,714,460 | A | 12/1987 | Calderon |
| 4,822,341 | A | 4/1989 | Colone |
| 4,838,864 | A | 6/1989 | Peterson |
| 4,957,484 | A | 9/1990 | Murtfeldt |
| 5,005,564 | A | 4/1991 | Grundei et al. |
| 5,069,662 | A | 12/1991 | Bodden |
| 5,092,844 | A | 3/1992 | Schwartz et al. |
| 5,097,840 | A | 3/1992 | Wallace et al. |
| 5,366,504 | A | 11/1994 | Andersen et al. |
| 5,391,143 | A | 2/1995 | Kensey |
| 5,484,412 | A | 1/1996 | Pierpont |
| 5,509,897 | A | 4/1996 | Twardowski et al. |
| 5,554,119 | A | 9/1996 | Harrison et al. |
| 5,558,642 | A | 9/1996 | Schweich, Jr. et al. |
| 5,702,364 | A | 12/1997 | Euteneuer |
| 5,716,340 | A | 2/1998 | Schweich, Jr. et al. |
| 5,817,046 | A | 10/1998 | Glickman |
| 5,836,912 | A | 11/1998 | Kusleika |
| 5,893,841 | A | 4/1999 | Glickman |
| 5,897,533 | A | 4/1999 | Glickman |
| 5,908,407 | A | 6/1999 | Frazee et al. |
| 5,919,163 | A | 7/1999 | Glickman |
| 5,921,913 | A | 7/1999 | Siess |
| 6,042,569 | A | 3/2000 | Finch, Jr. et al. |
| 6,139,517 | A | 10/2000 | Macoviak et al. |
| 6,152,945 | A | 11/2000 | Bachinski et al. |
| 6,165,196 | A | 12/2000 | Stack et al. |
| 6,179,796 | B1 | 1/2001 | Waldridge |
| 6,183,492 | B1 | 2/2001 | Hart et al. |
| 6,245,007 | B1 | 6/2001 | Bedingham et al. |
| 6,248,091 | B1 | 6/2001 | Voelker |
| 6,254,563 | B1 | 7/2001 | Macoviak et al. |
| 6,443,884 | B1 | 9/2002 | Miyawaki |
| 6,503,224 | B1 | 1/2003 | Forman et al. |
| 6,524,323 | B1 | 2/2003 | Nash et al. |
| 6,555,057 | B1 | 4/2003 | Bendera |
| 6,616,623 | B1 | 9/2003 | Kutushov |
| 6,635,068 | B1 | 10/2003 | Dubrul et al. |
| 6,699,231 | B1 | 3/2004 | Sterman et al. |
| 6,878,140 | B2 | 4/2005 | Barbut |
| 6,936,057 | B1 | 8/2005 | Nobles |
| 7,022,097 | B2 | 4/2006 | Glickman |
| 7,195,608 | B2 | 3/2007 | Burnett |
| 7,645,259 | B2 | 1/2010 | Goldman |
| 7,766,892 | B2 | 8/2010 | Keren et al. |
| 7,780,628 | B1 | 8/2010 | Keren et al. |
| 8,109,880 | B1 | 2/2012 | Pranevicius et al. |
| 8,126,538 | B2 | 2/2012 | Shuros et al. |
| 8,216,122 | B2 | 7/2012 | Kung |
| 8,480,555 | B2 | 7/2013 | Kung |
| 8,535,211 | B2 * | 9/2013 | Campbell ........... A61M 60/205 600/16 |
| 8,679,057 | B2 | 3/2014 | Fulton, III et al. |
| 9,179,921 | B1 | 11/2015 | Morris |
| 9,405,942 | B2 | 8/2016 | Liao et al. |
| 9,421,316 | B2 | 8/2016 | Leeflang et al. |
| 9,433,713 | B2 | 9/2016 | Corbett et al. |
| 9,486,566 | B2 | 11/2016 | Siess |
| 9,533,054 | B2 | 1/2017 | Yan et al. |
| 9,533,084 | B2 | 1/2017 | Siess et al. |
| 9,642,991 | B2 | 5/2017 | Eversull et al. |
| 9,669,142 | B2 | 6/2017 | Spanier et al. |
| 9,669,144 | B2 | 6/2017 | Spanier et al. |
| 9,675,739 | B2 | 6/2017 | Tanner et al. |
| 9,682,223 | B2 | 6/2017 | Callaghan et al. |
| 9,750,861 | B2 | 9/2017 | Hastie et al. |
| 9,770,543 | B2 | 9/2017 | Tanner et al. |
| 9,878,080 | B2 | 1/2018 | Kaiser et al. |
| 9,901,722 | B2 | 2/2018 | Nitzan et al. |
| 9,962,170 | B2 * | 5/2018 | Jansen ............... A61B 17/1622 |
| 10,149,684 | B2 | 12/2018 | Nitzan et al. |
| 10,154,846 | B2 | 12/2018 | Nitzan et al. |
| 10,195,405 | B2 | 2/2019 | Nitzan et al. |
| 10,207,086 | B2 | 2/2019 | Nitzan et al. |
| 10,226,604 | B2 | 3/2019 | Nitzan et al. |
| 10,226,605 | B2 | 3/2019 | Nitzan et al. |
| 10,245,363 | B1 | 4/2019 | Rowe |
| 10,285,708 | B2 | 5/2019 | Nitzan et al. |
| 10,300,254 | B2 | 5/2019 | Nitzan et al. |
| 10,639,460 | B2 | 5/2020 | Nitzan et al. |
| 10,653,871 | B2 | 5/2020 | Nitzan et al. |
| 10,709,878 | B2 | 7/2020 | Nitzan et al. |
| 10,912,873 | B2 | 2/2021 | Nitzan et al. |
| 10,926,069 | B2 | 2/2021 | Nitzan et al. |
| 10,960,189 | B2 | 3/2021 | Nitzan et al. |
| 11,007,353 | B2 | 5/2021 | Gerrans et al. |
| 11,166,730 | B2 | 11/2021 | Nitzan et al. |
| 11,179,550 | B2 | 11/2021 | Nitzan et al. |
| 11,179,551 | B2 | 11/2021 | Nitzan et al. |
| 11,179,552 | B2 | 11/2021 | Nitzan et al. |
| 11,357,959 | B2 | 6/2022 | Nitzan et al. |
| 11,406,393 | B2 | 8/2022 | Nitzan |
| 2002/0010418 | A1 | 1/2002 | Lary et al. |
| 2003/0093109 | A1 | 5/2003 | Mauch |
| 2003/0134416 | A1 | 7/2003 | Yamanishi et al. |
| 2003/0208097 | A1 | 11/2003 | Aboul-Hosn et al. |
| 2004/0006306 | A1 | 1/2004 | Evans et al. |
| 2004/0064091 | A1 | 4/2004 | Keren et al. |
| 2004/0147871 | A1 | 7/2004 | Burnett |
| 2004/0210296 | A1 | 10/2004 | Schmitt et al. |
| 2004/0230181 | A1 | 11/2004 | Cawood |
| 2005/0085772 | A1 | 4/2005 | Zafirelis et al. |
| 2005/0228474 | A1 | 10/2005 | Laguna |
| 2005/0251180 | A1 | 11/2005 | Burton et al. |
| 2006/0030814 | A1 | 2/2006 | Valencia et al. |
| 2006/0064059 | A1 | 3/2006 | Gelfand et al. |
| 2006/0100658 | A1 | 5/2006 | Obana et al. |
| 2006/0161095 | A1 | 7/2006 | Aboul-Hosn et al. |
| 2006/0178604 | A1 | 8/2006 | Alderman |
| 2007/0055299 | A1 | 3/2007 | Ishimaru et al. |
| 2007/0282303 | A1 | 12/2007 | Nash et al. |
| 2007/0282382 | A1 | 12/2007 | Shuros et al. |
| 2008/0009719 | A1 | 1/2008 | Shuros et al. |
| 2008/0015628 | A1 | 1/2008 | Dubrul et al. |
| 2008/0071135 | A1 | 3/2008 | Shaknovich |
| 2008/0097412 | A1 | 4/2008 | Shuros et al. |
| 2008/0103573 | A1 | 5/2008 | Gerber |
| 2008/0140000 | A1 | 6/2008 | Shuros et al. |
| 2008/0294228 | A1 | 11/2008 | Brooke et al. |
| 2009/0018526 | A1 | 1/2009 | Power et al. |
| 2009/0069829 | A1 * | 3/2009 | Shturman .......... A61B 17/3207 606/159 |
| 2009/0112184 | A1 | 4/2009 | Fierens et al. |
| 2009/0131785 | A1 | 5/2009 | Lee et al. |
| 2010/0168649 | A1 | 7/2010 | Schwartz et al. |
| 2010/0179389 | A1 | 7/2010 | Moroney, III et al. |
| 2010/0280451 | A1 | 11/2010 | Teeslink et al. |
| 2010/0318114 | A1 | 12/2010 | Pranevicius et al. |
| 2011/0004046 | A1 | 1/2011 | Campbell et al. |
| 2011/0092955 | A1 | 4/2011 | Purdy et al. |
| 2011/0257462 | A1 | 10/2011 | Rodefeld et al. |
| 2011/0276023 | A1 | 11/2011 | Leeflang et al. |
| 2011/0282274 | A1 | 11/2011 | Fulton, III |
| 2011/0295302 | A1 | 12/2011 | Mohl |
| 2012/0029466 | A1 | 2/2012 | Callaghan et al. |
| 2012/0157913 | A1 | 6/2012 | Aziz et al. |
| 2012/0178986 | A1 | 7/2012 | Campbell et al. |
| 2012/0259215 | A1 | 10/2012 | Gerrans et al. |
| 2013/0096476 | A1 | 4/2013 | Rogachevsky |

(56) References Cited

U.S. PATENT DOCUMENTS

| | | |
|---|---|---|
| 2013/0096494 A1 | 4/2013 | Kassab |
| 2013/0138041 A1 | 5/2013 | Smisson, III et al. |
| 2013/0177432 A1 | 7/2013 | Toellner et al. |
| 2013/0237954 A1 | 9/2013 | Shuros et al. |
| 2013/0245607 A1 | 9/2013 | Eversull et al. |
| 2013/0303831 A1* | 11/2013 | Evans .............. A61M 60/237 600/16 |
| 2013/0303969 A1 | 11/2013 | Keenan et al. |
| 2013/0317535 A1 | 11/2013 | Demmy |
| 2013/0331814 A1 | 12/2013 | Fulton, III et al. |
| 2013/0338559 A1 | 12/2013 | Franano et al. |
| 2014/0010686 A1 | 1/2014 | Tanner et al. |
| 2014/0128659 A1 | 5/2014 | Heuring et al. |
| 2014/0142616 A1 | 5/2014 | Smith |
| 2014/0155815 A1 | 6/2014 | Fulton, III et al. |
| 2014/0220617 A1 | 8/2014 | Yung et al. |
| 2014/0243790 A1 | 8/2014 | Callaghan et al. |
| 2014/0249386 A1 | 9/2014 | Caron et al. |
| 2014/0296615 A1 | 10/2014 | Franano |
| 2014/0303461 A1 | 10/2014 | Callaghan et al. |
| 2014/0336551 A1 | 11/2014 | Mantese et al. |
| 2014/0358036 A1 | 12/2014 | Holmes |
| 2015/0051634 A1 | 2/2015 | Kravik et al. |
| 2015/0157777 A1 | 6/2015 | Tuval et al. |
| 2015/0164662 A1 | 6/2015 | Tuval |
| 2015/0238671 A1 | 8/2015 | Mesallum |
| 2015/0283360 A1 | 10/2015 | Kelly |
| 2015/0306360 A1* | 10/2015 | Tischler ............ A61M 25/0043 604/218 |
| 2015/0343136 A1 | 12/2015 | Nitzan et al. |
| 2015/0343186 A1 | 12/2015 | Nitzan et al. |
| 2016/0022890 A1 | 1/2016 | Schwammenthal et al. |
| 2016/0045203 A1 | 2/2016 | Pollock |
| 2016/0051741 A1 | 2/2016 | Schwammenthal et al. |
| 2016/0129266 A1 | 5/2016 | Schmidt |
| 2016/0166463 A1 | 6/2016 | Douglas et al. |
| 2016/0169630 A1 | 6/2016 | Augustine et al. |
| 2016/0213826 A1* | 7/2016 | Tanner .............. A61M 60/829 |
| 2016/0331378 A1 | 11/2016 | Nitzan et al. |
| 2017/0014563 A1 | 1/2017 | Khir |
| 2017/0095395 A1 | 4/2017 | Wennen et al. |
| 2017/0197021 A1 | 7/2017 | Nitzan et al. |
| 2017/0224512 A1 | 8/2017 | Hingston |
| 2017/0319764 A1 | 11/2017 | Tanner et al. |
| 2018/0012630 A1 | 1/2018 | Thomee et al. |
| 2018/0125499 A1 | 5/2018 | Nitzan et al. |
| 2018/0126130 A1 | 5/2018 | Nitzan et al. |
| 2018/0146968 A1 | 5/2018 | Nitzan et al. |
| 2018/0169312 A1* | 6/2018 | Barry .............. A61M 60/414 |
| 2018/0185622 A1 | 7/2018 | Nitzan et al. |
| 2018/0193614 A1 | 7/2018 | Nitzan et al. |
| 2018/0193615 A1 | 7/2018 | Nitzan et al. |
| 2018/0193616 A1 | 7/2018 | Nitzan et al. |
| 2018/0250456 A1* | 9/2018 | Nitzan .............. A61B 5/02152 |
| 2018/0303986 A1 | 10/2018 | Meacham |
| 2019/0014991 A1 | 1/2019 | Maki et al. |
| 2019/0046706 A1 | 2/2019 | Aboul-Hosn et al. |
| 2019/0046707 A1 | 2/2019 | Aboul-Hosn et al. |
| 2019/0083761 A1 | 3/2019 | Nitzan et al. |
| 2019/0117943 A1 | 4/2019 | Nitzan et al. |
| 2019/0117944 A1 | 4/2019 | Nitzan et al. |
| 2019/0126014 A1 | 5/2019 | Kapur et al. |
| 2019/0167878 A1 | 6/2019 | Rowe |
| 2019/0223877 A1 | 7/2019 | Nitzan et al. |
| 2019/0366063 A1 | 12/2019 | Nitzan et al. |
| 2020/0016383 A1 | 1/2020 | Nitzan et al. |
| 2020/0030586 A1 | 1/2020 | Nitzan et al. |
| 2020/0030587 A1 | 1/2020 | Nitzan et al. |
| 2020/0046372 A1 | 2/2020 | Nitzan |
| 2020/0206485 A1 | 7/2020 | Nitzan et al. |
| 2020/0230380 A1 | 7/2020 | Nitzan et al. |
| 2020/0230381 A1 | 7/2020 | Nitzan et al. |
| 2020/0261706 A1 | 8/2020 | Nitzan et al. |
| 2020/0268951 A1 | 8/2020 | Nitzan et al. |
| 2020/0268952 A1 | 8/2020 | Nitzan et al. |
| 2020/0268954 A1 | 8/2020 | Nitzan et al. |
| 2020/0269025 A1 | 8/2020 | Nitzan et al. |
| 2020/0276369 A1 | 9/2020 | Nitzan et al. |
| 2020/0306436 A1 | 10/2020 | Tanner et al. |
| 2020/0397963 A1 | 12/2020 | Nitzan et al. |
| 2021/0121678 A1 | 4/2021 | Nitzan et al. |
| 2021/0378676 A1 | 12/2021 | Keating et al. |
| 2021/0378677 A1 | 12/2021 | Keating et al. |
| 2021/0378678 A1 | 12/2021 | Keating et al. |
| 2021/0379329 A1 | 12/2021 | Keating et al. |
| 2022/0039803 A1 | 2/2022 | Nitzan et al. |
| 2022/0104827 A1 | 4/2022 | Keating et al. |
| 2022/0104828 A1 | 4/2022 | Keating et al. |
| 2022/0218360 A1 | 7/2022 | Nitzan et al. |
| 2022/0218961 A1 | 7/2022 | Nitzan et al. |
| 2022/0280761 A1 | 9/2022 | Nitzan et al. |
| 2022/0280762 A1 | 9/2022 | Nitzan et al. |
| 2022/0331510 A1 | 10/2022 | Amstutz et al. |

FOREIGN PATENT DOCUMENTS

| | | |
|---|---|---|
| EP | 2353503 A1 | 8/2011 |
| EP | 2353632 A1 | 8/2011 |
| EP | 2497524 A1 | 9/2012 |
| EP | 2637927 B1 | 9/2013 |
| WO | 89/04193 A1 | 5/1989 |
| WO | 2000/024337 A2 | 5/2000 |
| WO | 01/013983 A2 | 3/2001 |
| WO | 2012/135834 A2 | 10/2012 |
| WO | 2013/025826 A1 | 2/2013 |
| WO | 2013/061281 A1 | 5/2013 |
| WO | 2014/141284 A2 | 9/2014 |
| WO | 2015/186003 A2 | 12/2015 |
| WO | 2017/087556 A1 | 5/2017 |
| WO | 2018/158636 A1 | 9/2018 |
| WO | 2018172848 A2 | 9/2018 |
| WO | 2018/202776 A1 | 11/2018 |
| WO | 2019/027380 A1 | 2/2019 |
| WO | 2020/174285 A2 | 9/2020 |

OTHER PUBLICATIONS

Moscucci, 2014, Section III Hemodynamic principles 10 Pressure measurement, 223-244 in Grossman & Baim's Cardiac Catheterization, Angiography, and Intervention 8 Ed.

Shimizu, 2014, Embolization of a fractured central venous catheter placed using the internal jugular apporach, Int J Surg Case Rep 5:219.

Stone, 2010, The effect of rigid cervical collars on internal jugular vein dimensions, Acad Emerg Med 17(1):100-102.

Swan, 1970, Catheterization of the Heart in Man with Use of a Flow-directed Balloon-tipped Catheter, NEJM 283(9):447-451.

Yancy, 2013, 2013 ACCF/AHA Guideline for the Management of Heart Failure, Circulation 128(16):e240-e327.

Biran, 2017, Heparin coatings for improving blood compatibility of medical devices, Adv Drug Delivery Rev, 112:12-23.

Shimizu, 2014, Embolization of a fractured central venous catheter placed using the internal jugular apporach, Int J Surg Case Rep 5:219-221.

Webb, 2012, Roughness parameters for standard description of surface nanoarchitecture, Scanning 34:257-263.

Blitz, 2014, Pump thrombosis—a riddle wrapped in a mystery inside an enigma, Ann Cardiothorac Surg, 3(5):450-471.

Chikly, 2005, Manual techniques addressing the lymphatic system: origins and development, JAOA 105(10):457-464.

Ratnayake, 2018, The Anatomy and physiology of the terminal thoracic duct and ostial valve in health and disease: potential implications for intervention, J Anat 233:1-14.

Tchantchaleishvili, 2014, Evaluation and treatment of pump thrombosis and hemolysis, Ann Cardiothorac Surg, 3(5):490-495.

\* cited by examiner

INTRAVASCULAR CATHETERS

CROSS-REFERENCE TO RELATED APPLICATION

This application is a national stage entry of PCT/IB2019/000139, filed Feb. 12, 2019, which claims priority to U.S. Provisional Application No. 62/629,914, filed Feb. 13, 2018, the contents of which are incorporated by reference.

FIELD OF THE INVENTION

The disclosure relates to intravascular catheters having a purge system, and optionally, a guidewire lumen through an impeller.

BACKGROUND

Congestive heart failure is the result of a weakened heart. As blood flow out of the heart slows, blood returning to the heart backs up and increases in pressure in the veins, inhibiting drainage from the lymphatic system, causing congestion in the body, resulting in edema. Edema may manifest as visible swelling in a person's legs and ankles, and can be present in other parts of the body as well. Sometimes fluid collects in the lungs and interferes with breathing. This is called pulmonary edema and can be particularly distressing. Heart failure also affects the ability of the kidneys to dispose of sodium and water and the retained water also contributes to the edema.

Congestive heart failure and edema may potentially be treated using drugs or medical devices. For example, intravascular catheters may potentially be used to assist in draining the lymphatic system or pumping blood. Such catheters may be designed with mechanical components such as pumps or inflatable balloons.

Intravascular treatment using catheters with mechanical components presents a variety of challenges. For example, intravascular catheters having mechanical parts typically have joints or different connection points that couple different mechanical elements of the catheter. Those joints or connection points serve as locations where body fluid, e.g., blood and/or lymph, can enter or leak into the catheter. Blood and lymph contain live cells, dead cells, fragments of lipids, free nucleic acids, and other materials. Those materials can interfere with the reliable functioning of an intravascular device, particularly operation of rotating mechanical parts. Additionally, the body fluid that enters the catheter could possibly travel to a proximal portion of the catheter outside of the patient's body, where it could leak out of the catheter, creating an unsterile situation for the patient and care providers.

SUMMARY

The disclosure provides intravascular catheters having mechanical components, e.g., an impeller and/or drive shaft, and a purge system. The purge system operates to exclude biological fluids and materials from the catheter and mechanical components operating within the catheter. In that manner, the intravascular catheters of the invention are able to prevent body fluid from entering the catheter, ensuring smooth and efficient operation of the mechanical parts, e.g., impeller and drive shaft, within the catheter while also preventing the patient's body fluid from travelling to a proximal portion of the catheter outside of the patient's body, where it could leak out of the catheter.

In certain aspects, a distal portion of a catheter can be dimensioned for insertion into a blood vessel. The catheter can be equipped with an impeller coupled to a rotating drive shaft. As will be discussed below, the catheter can have additional features to restrict flow or to aid flow, such as inflatable balloons or pumps. The catheter is also equipped with a purge system that can use, for example, a purge fluid to prevent blood, lymph, or other biological materials from entering mechanical parts of the catheter, e.g., motor, impeller, driver shaft, etc. The purge system of the disclosure excludes bodily fluids from the catheter both while the devices are not deployed or not operating and while such devices are deployed or operating. For example, the catheter can be purged by a purge fluid under hydrostatic pressure that excludes bodily fluid while a physician is navigating the catheter to the desired location. In embodiments in which the catheter includes a device such as an impeller, centrifugal force can be exploited to wash the impeller and associated motor during operation of the device.

In certain embodiments, the device includes a catheter dimensioned for insertion into a bodily lumen, a porous drive shaft extending from a motor and through the catheter, in which a portion of the drive shaft is housed within a tube comprising one or more through holes, and an infusion channel in fluid communication with the porous drive shaft and arranged such that purge fluid is discharged through the porous drive shaft and through the through holes of the tube. A proximal end of the tube includes a proximal sealed connection around the drive shaft. Operation of the motor rotates the drive shaft within the tube. A distal end of the tube may include a distal sealed connection around the drive shaft. The device may further include one or more inflatable balloons disposed along the catheter, each in fluid communication with an inflation lumen extending along the catheter.

When the motor is not rotating, a static pressure of the purge fluid prevents bodily fluid from entering the housing. When the motor is rotating, the purge fluid is subject to centrifugal force along the drive shaft preventing bodily fluid from approaching the proximal portion of the catheter. The motor may include a rotor disposed within a stator in a housing at a proximal portion of the catheter. The porous drive shaft may be coupled to, and extending from, the rotor.

Preferably, when the impeller is inserted into vasculature of a patient, the proximal sealed connection, the tube, and/or the distal sealed connection separate the purge fluid within the porous drive shaft from blood within the catheter outside of the tube.

In some embodiments, the impeller has one or more blades disposed along an impeller shaft coupled to the drive shaft, in which the impeller shaft has an impeller shaft lumen therethrough and one or more holes along a side of the impeller shaft such that rotation of the impeller in a liquid subjects the liquid to centrifugal force at the one or more holes. When rotating, the purge fluid is driven by centrifugal force outward through the through-holes along the impeller shaft such that the purge fluid continually washes the impeller. In certain embodiments, when the impeller is disposed within vasculature of a patient and the motor is operated, the impeller pumps blood and the purge fluid rinses at least a portion of the impeller.

The disclosure additionally provides intravascular catheters with treatment devices such as impellers that can be delivered over, and operated over, a guidewire, to aid in operating intravascular treatment devices in the correct location and orientation within a body. That is, in certain aspects, the invention provides intravascular impeller based devices in which the impeller has a guidewire channel there through and the impeller can operate while a guidewire is extended through the impeller within the guidewire channel. As discussed herein, catheters of the disclosure may include additional features that operate to restrict flow, to assist flow, or both. A physician can navigate a guidewire to an intended treatment location and manually refine the positioning of the guidewire. The device is loaded onto the guidewire via the guidewire channel that passes through the impeller. The device is then pushed over the guidewire to the intended location. Exemplary embodiments include a catheter with one or more flow restrictors, such as inflatable balloons, and a pump or impeller, in which the flow restrictors create a low pressure zone around an output of a thoracic duct while the impeller aids in draining the lymphatic system. The inflatable balloons and the impeller can be deployed and operated, respectively, even while the guidewire extends through a guidewire lumen that passes through the impeller.

By including over-the-wire treatment devices on an intravascular catheter, in which those devices can be deployed and operated while the catheter is being navigated over a guidewire, the disclosure provides intravascular treatment devices that can be delivered to, and oriented correctly at, a desired location within a patient. The guidewire functionality assists greatly in properly positioning the treatment devices.

Aspects of the invention provide a device that includes an impeller dimensioned for insertion into vasculature of a patient, a guidewire lumen extending through the impeller, and a drive mechanism operable to rotate the impeller while the impeller is in the vasculature with a guidewire extending through the lumen. The drive mechanism may include a hollow driveshaft extending proximally from the impeller to a motor. The hollow driveshaft may extend through a catheter having a proximal portion and a distal portion, in which the impeller is distal to the distal portion and the motor is proximal to the proximal portion. In some embodiments, the motor sits in a housing connected to the proximal portion of the catheter. The motor may include a stator housed within the housing and a rotor disposed within the stator, wherein the guidewire lumen extends through the impeller, through the driveshaft, and through the rotor.

In certain embodiments, the guidewire lumen opens to a tapered port at a proximal portion of the housing. The device may include a hollow atraumatic tip extending distally from the impeller.

In some embodiments, the hollow driveshaft extends through an extended catheter, in which the impeller is disposed at a distal portion of the catheter and the motor is disposed at a proximal portion of the catheter. The device may include an impeller housing connected to the distal portion of the catheter and may include at least one inlet port proximal to the impeller and at least one outlet port distal to the impeller, wherein rotation of the impeller impels liquid through the impeller housing. The device may further include an expandable member on the distal portion of the catheter and at least one inflation lumen extending through the catheter.

In some embodiments, the expandable member comprises a substantially toroidal balloon connected to the catheter or impeller housing by an expandable membrane. When the catheter is inserted over a guidewire into the vasculature, the balloon can be inflated and the impeller can be rotated by operation of the motor while the guidewire extends through the device.

By including a purge system, devices of the catheter operate reliably and operation of those device is not interfered with by cells, dead cell fragments and other debris found in bodily fluids. Thus intravascular catheters of the disclosure are easily positioned and operate reliably. The catheters may include treatment devices that are particularly suited to the treatment of edema or congestive heart failure, such as mechanisms that aid in draining a lymphatic system. Since the guidewire aids in positioning the device, and the purge system facilitates reliable operation, intravascular catheters of the disclosure may be used to treat heart failure and edema with positional accuracy and material reliability.

In certain embodiments, the impeller and the drive shaft may define or include a guidewire lumen that extends through the impeller and the drive shaft. The guidewire lumen preferably extends through the motor, such that when the device is inserted into vasculature of a patient over a guidewire, operation of the motor rotates the impeller within the vasculature while the guidewire extends through the guidewire lumen. The device may be operable when the guidewire extends distally out of a distal tip of device. In such embodiments, when the device is inserted into the vasculature of the patient over the guidewire: the purge fluid continually purges the catheter when the motor is operated; and the purge fluid continually purges the catheter when the motor is not operated.

Preferably, when the impeller is inserted into vasculature of a patient, the purge fluid purges the catheter by hydrostatic pressure while the motor is not operated and the purge fluid purges the catheter by centrifugal force while the motor is operated.

In related aspects, the invention provides a device having an impeller disposed at a distal portion of a catheter and dimensioned for insertion into vasculature of a patient. When the impeller is inserted into the vasculature of a patient, a purge fluid purges the catheter by hydrostatic pressure while the impeller is not being rotated and the purge fluid purges the catheter by centrifugal force while the impeller is being rotated.

DETAILED DESCRIPTION

Figure 1:
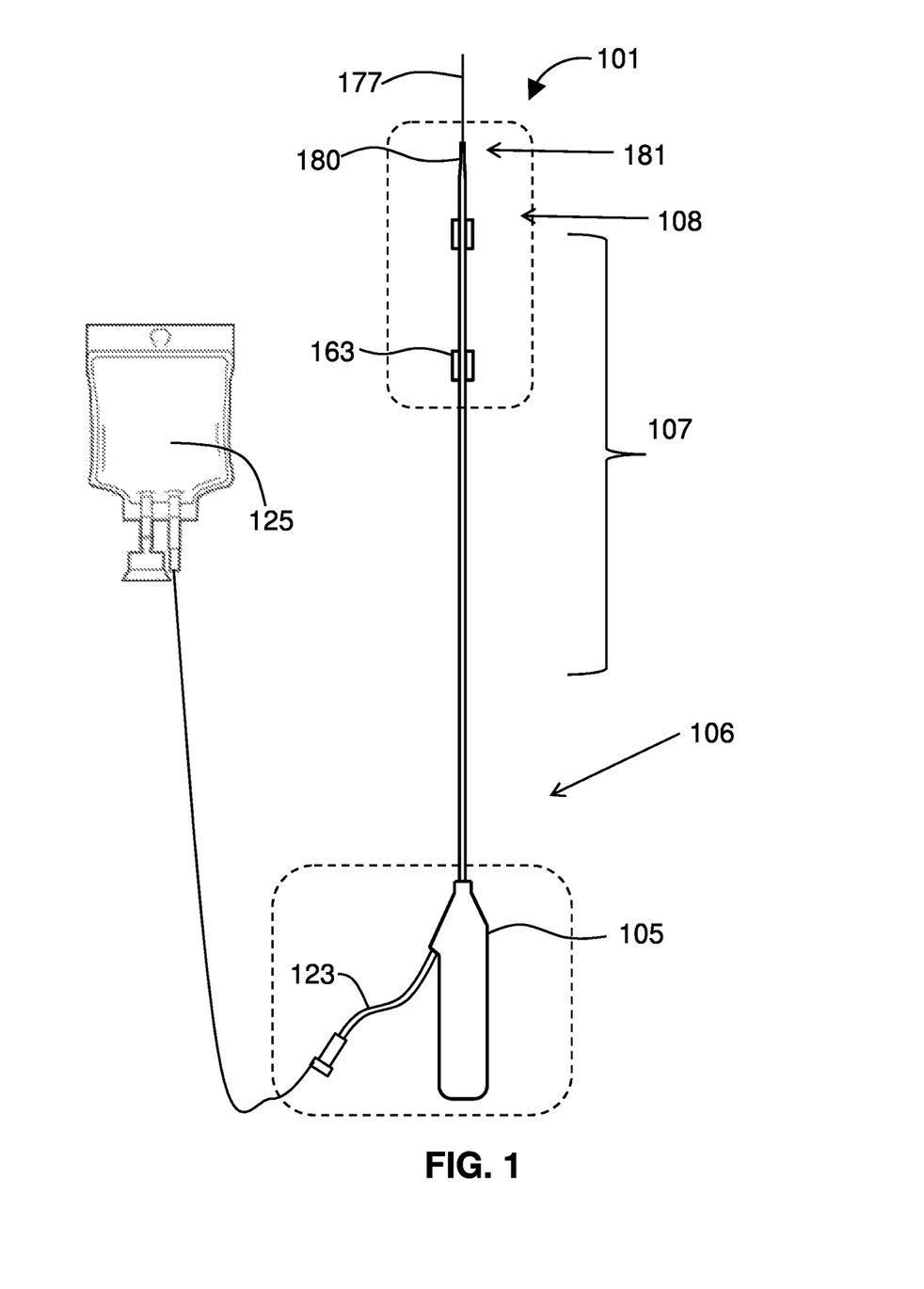
FIG. 1 shows a device of the disclosure.

FIG. 1 shows a device 101 with an extended catheter 107, having a proximal portion 106 and a distal portion 108, extending from a housing 105. The catheter 107 is dimensioned for insertion into a bodily lumen, such as a vein of a patient. At a distal portion 108 of the catheter 107, a flexible, atraumatic tip 180 extends past the distal portion 108 of the catheter 107, terminating at a distal tip 181. A guidewire 177 is shown, extending from the distal tip 181 of the device 101.

An infusion channel 123 enters the housing 105, allowing a purge fluid 125 to enter the catheter by the infusion channel 123. As discussed in greater detail below, the device 101 may include one or more expandable members 163, e.g., located at the distal portion 108 of the catheter 107.

Figure 2:
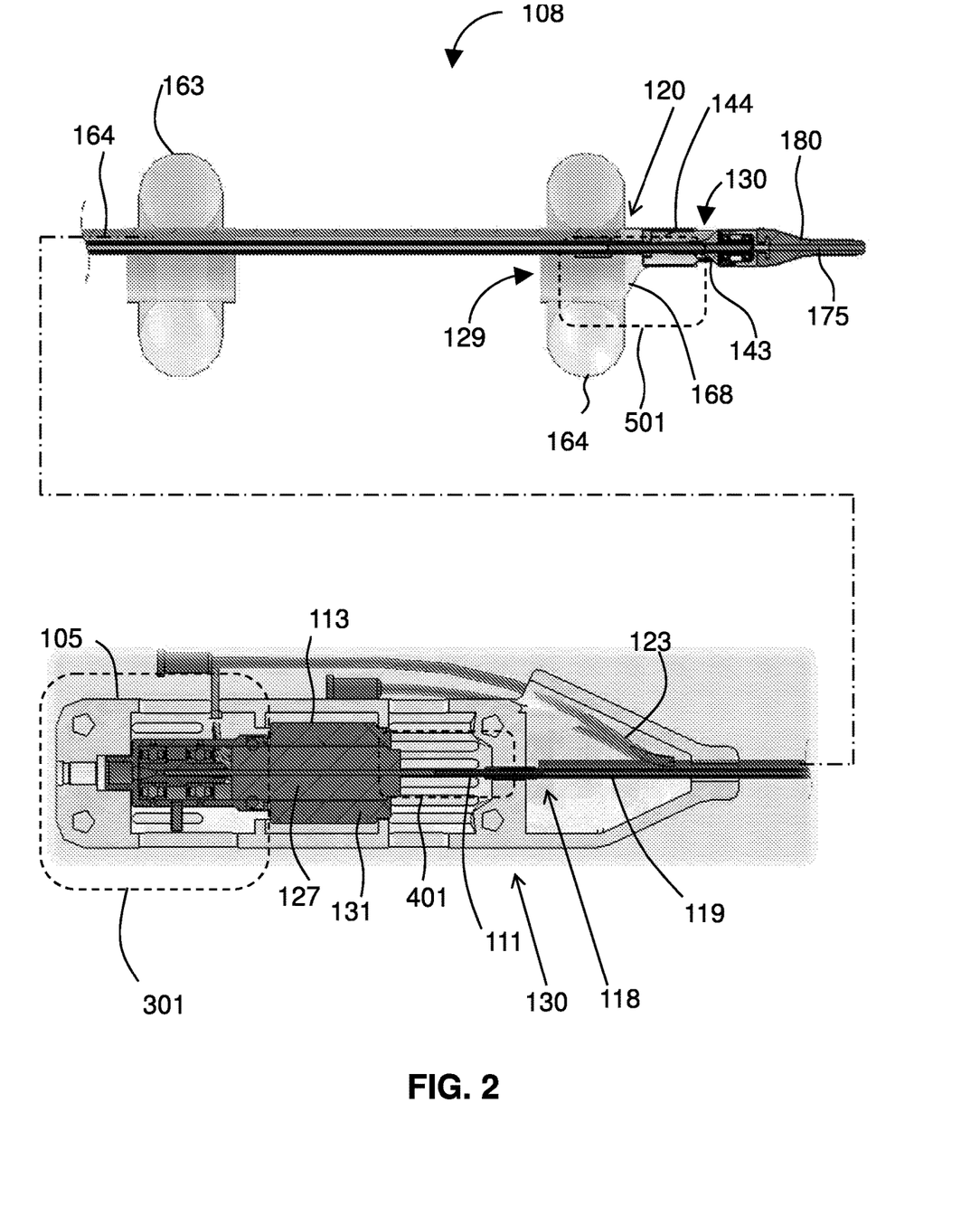
FIG. 2 gives a cutaway view of a housing and a distal portion of a catheter of the device.

FIG. 2 gives a cutaway view of the housing 105 and the distal portion 108 of the catheter 107. The motor housing 105 houses a drive mechanism 130. Embodiments of the drive mechanism 130 include a motor 113 having a rotor 127 disposed within a stator 131. A porous drive shaft 111 extends from a motor 113 through the catheter 107. At least a portion of the drive shaft 111 is housed within a tube 119. The motor 113 comprises a rotor 127 disposed within a stator 131 in a housing 105 at a proximal portion 106 of the catheter 107.

The device 101 includes a porous drive shaft 111 extending from a motor 113 through the catheter 107. A portion of the drive shaft 111 is housed within a tube 119 that may extend from the housing 105 to the distal portion 108.

At the housing 105, an infusion channel 123 is in fluid communication with the porous drive shaft 111 and arranged such that a purge fluid 125 is discharged through the porous drive shaft 111 and towards the distal portion 108.

The distal portion 108 includes the distal end 120 of the tube 119, with an expandable membrane 168 and balloon 164 disposed about the catheter. Distal to the distal end 120 of the tube 119 is an impeller housing 144, housing an impeller 143, and a hollow atraumatic tip 180. The balloon 164 (when inflated), the expandable membrane 168 (which expands when the balloon 164 is inflated), and the impeller housing 144 collectively provide and include at least one inlet port 129 and outlet port 130, which provide a passage through the membrane 168 and impeller housing 144 through which the impeller 143 can pump a fluid such as blood.

The tube 119 extends from a proximal end 118 of the tube 119 (in the housing 105) to a distal end of 120 of the tube 119 (on the distal portion 108 of the catheter 107). The tube 119 surrounds a length of the hollow driveshaft 111 extending from the drive mechanism 130. Specifically, the hollow driveshaft 111 extends from the rotor 127 mounted within the stator 131.

The distal portion 108 includes the impeller 143, dimensioned for insertion into vasculature of a patient. A guidewire lumen 175 extends through the impeller 143. The drive mechanism 130 is operable to rotate the impeller 143 while the impeller 143 is in the vasculature with a guidewire extending through the guidewire lumen 175. Features and devices of the invention may be used in a variety of catheters and treatment devices and may, for example, be incorporated into any of those devices described in U.S. Pat. No. 9,901,722; U.S. Pub. 2016/0331378; U.S. Pub. 2015/0343186; U.S. Pub. 2015-0343136; U.S. Pub. 2017/0197021; Int'l Patent Appl. Pub. WO 2016/181217; Intl Patent Appl. Pub. WO 2015/186005; and Int'l Patent Appl. Pub. WO 2015/186003, the contents of each of which are incorporated by reference.

FIG. 2 includes boxes to call out a proximal section 301 of the device 101, a middle section 401 of the device 101, and a distal section 501 of the device 101.

Figure 3:
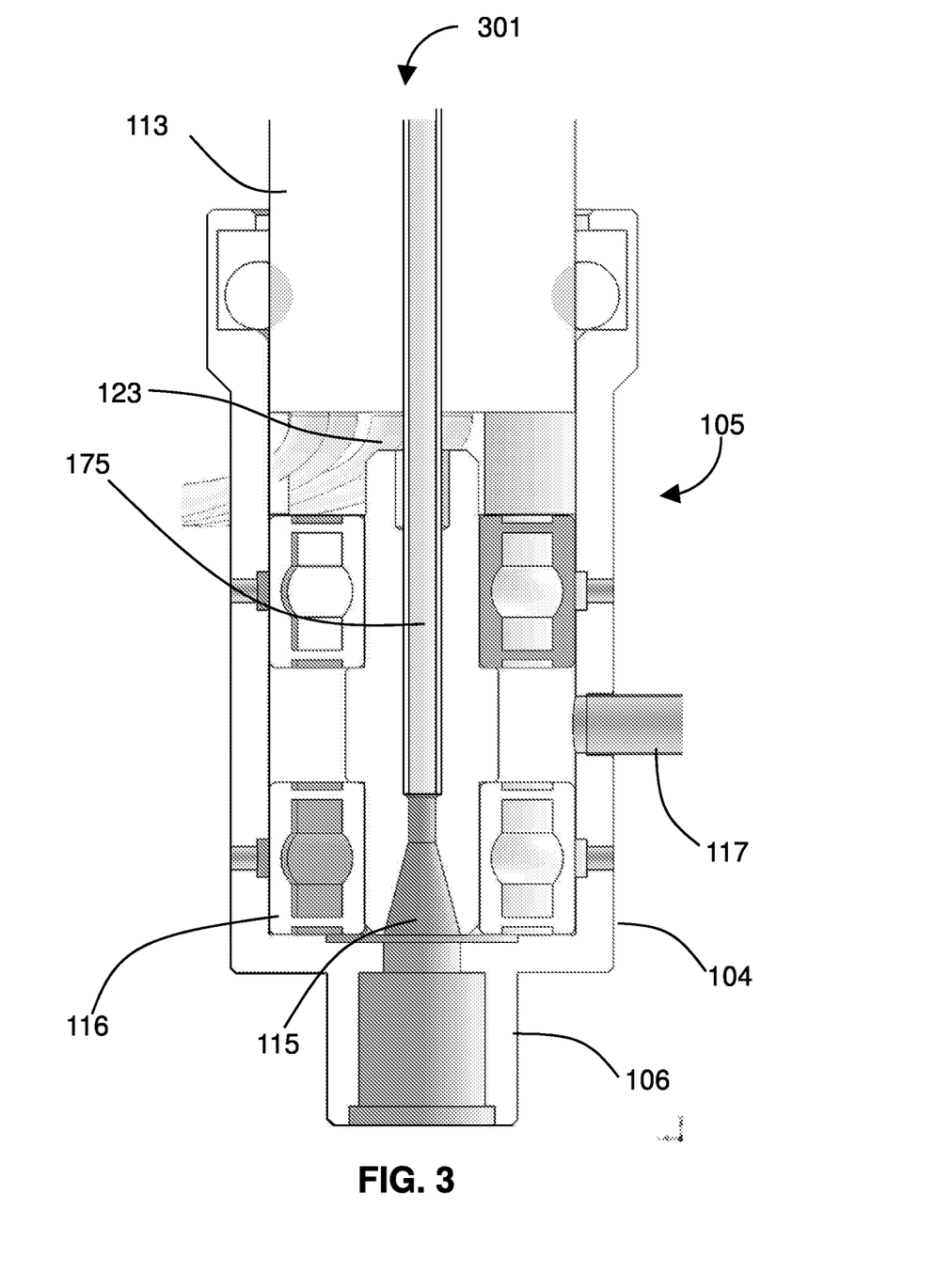
FIG. 3 shows the proximal section of the device.

FIG. 3 shows the proximal section 301 of the device 101. The guidewire lumen 175 extends through the housing 105. A drainer 117 is in fluid communication with an interior space of the housing. At a proximal portion 104 of housing 105, is a Luer 106 providing access to a tapered port 115 that can guide a guidewire into the guidewire lumen 175. One or more sealed bearings 116 may be included to allow rotation of the driveshaft and minimize vibrations of the motor 113. The infusion channel 123 allows purge fluid 125 to enter the catheter 107.

Figure 4:
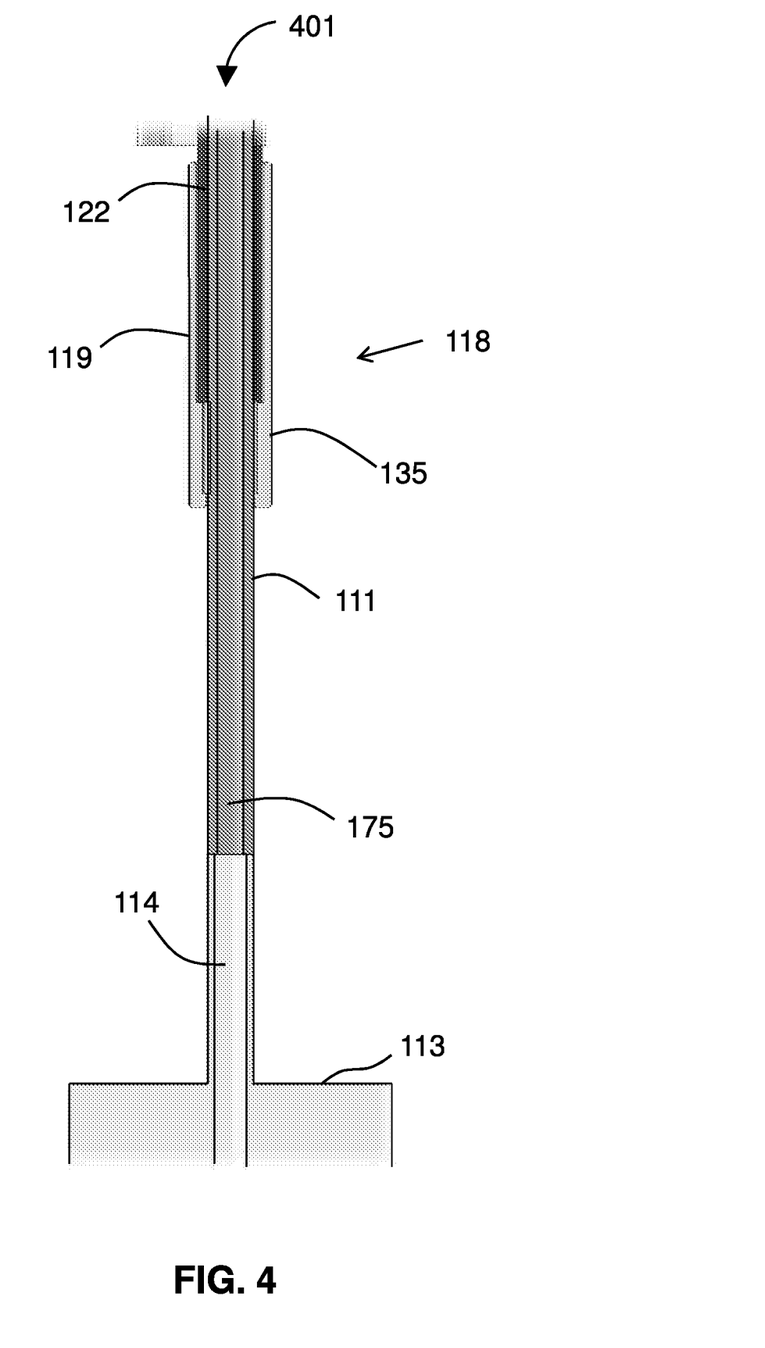
FIG. 4 shows the middle section of the device.

FIG. 4 shows the middle section 401 of the device 101. A proximal end 118 of tube 119 includes a proximal tube seal 135 (a distal tube seal 139 is located at the other end) to seal the tube 119 around the drive shaft 111. The guidewire lumen 175 extends through the drive shaft 111, which connects to the motor 113 via a motor shaft 114. The tube 119 surrounds a sleeve 122 which sits around the drive shaft. The proximal end 118 of the tube 119 includes a proximal tube seal 135 around the drive shaft 111. Operation of the motor 113 rotates the drive shaft 111 within the tube 119.

Figure 5:
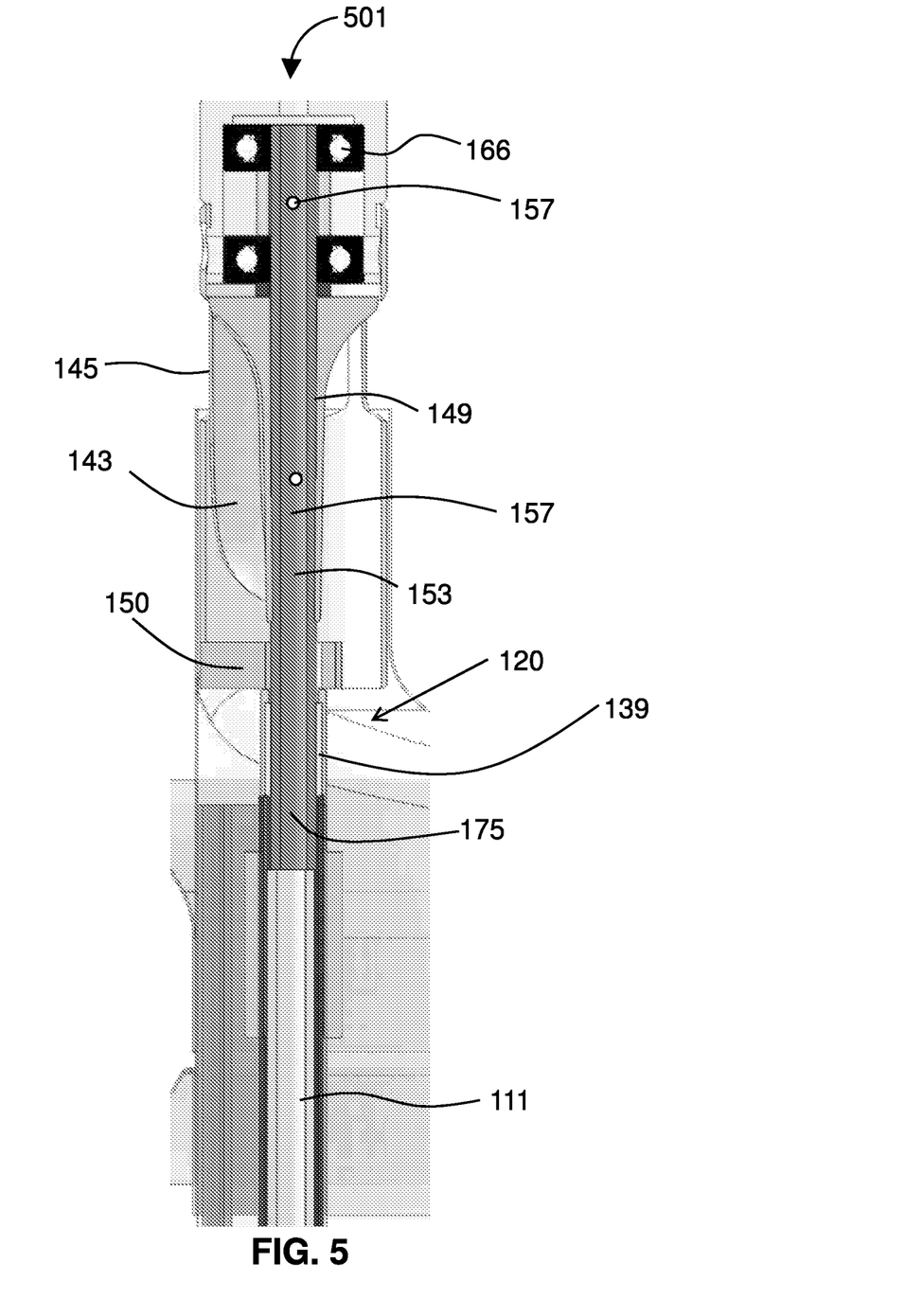
FIG. 5 shows the distal section of the device.

FIG. 5 shows the distal section 501 of the device 101. The hollow drive shaft 111 terminates at the impeller 143 on an impeller shaft 149. The impeller shaft 149 has one or more through holes 157. The impeller shaft 149 may be seated in one or more distal sealed bearing 166. Extending through the impeller shaft 149 is an impeller shaft lumen 153, which is in fluidic communication with a surrounding environment at least through the one or more through holes 157. The tube 119 ends at the distal tube end 120, where it forms a distal tube seal 139 around the hollow drive shaft 111. The hollow drive shaft 111 and the impeller shaft lumen 153 cooperate to define or include at least a portion of the guidewire lumen 175. The impeller 143 is seated within the impeller housing 144 by means of one or more support rings 150, which may be, for example, open central rings supported within an outer ring by multiple spokes. The impeller 143 has one or a plurality of blades 145 to impel fluid through the impeller housing 144 when the impeller 143 rotates.

With reference back to FIGS. 1-5, the purge fluid 125 may be supplied in a reservoir, e.g., an IV bag, that may hang from a rack to be gravitationally higher than the device 101 when the device 101 is used bedside in a clinical setting. The porous drive shaft 111 is coupled to, and extends from, the rotor 127 of the motor 113. The porous, hollow drive shaft 111 that rotates when the motor 113 operates influences the fate of purge fluid 125 that enters the catheter 107 through the infusion channel 123. When the motor 113 is not rotating, a static pressure of the purge fluid 125 prevents bodily fluid from entering the housing 105. When the motor 113 is rotating, the purge fluid 125 is subject to centrifugal force along the drive shaft 111 preventing bodily fluid from approaching the proximal portion 106 of the catheter 107.

Components described herein thus provide a purge system for an intravascular treatment catheter, particularly for catheters that use rotational mechanisms such as impellers or ablation tools or for over-the-wire catheters that provide instruments that can be inserted into vasculature of a patient over a guidewire. Any suitable purge fluid 125, such as saline, may be used. The described components and features cooperate to prevent bodily fluids from entering the catheter when parts of the catheter are stationary and also when mechanical parts are operating.

In certain embodiments, when the impeller 143 is inserted into vasculature of a patient, the proximal tube seal 135, the tube 119, and/or the distal tube seal 129 separate the purge fluid 125 within the porous drive shaft 111 from blood within the catheter 107 outside of the tube 119. The impeller 143 may include one or more blades 145 disposed along an impeller shaft 149 coupled to the drive shaft 111, in which the impeller shaft 149 has an impeller shaft lumen 153 therethrough and one or more through-holes 157 along a side of the impeller shaft 149 such that rotation of the impeller 143 in a liquid subjects the liquid to centrifugal force at the one or more holes 157. That is, when the impeller 143 is disposed within vasculature of a patient and the motor 113 is operated, the impeller 143 pumps blood and the purge fluid 125 rinses at least a portion of the impeller 143. In such scenario, purge fluid in the catheter 107 (e.g., that flowed in under gravity while the impeller was not operating) would be driven out through the through-holes 157 while the motor 113 operates, thereby securely preventing any bodily fluid from entering the device 101.

The purge system may have particular applicability on devices used in different bodily systems, such as the circulatory system and the lymphatic system. E.g., the purge fluid prevents blood from entering the device 101, so that if the device 101 is subsequently entered into a thoracic duct, blood is not brought into that area.

In certain depicted embodiments, the device 101 includes one or more inflatable balloons 163 disposed along the catheter 107, each in fluid communication with an inflation lumen 164 extending along the catheter 107.

In certain embodiments, the device 101 is designed as an over-the-wire device in that it can be delivered to a location in the vasculature of a patient by following a guidewire that has been navigated to the intended location. Preferably, the impeller 143 and the drive shaft 111 define or include a guidewire lumen 175 that extends through the impeller 143 and the drive shaft 111.

In some embodiments (see, e.g., FIG. 2), the guidewire lumen 175 extends through the motor 113. When the device 101 is inserted into vasculature of a patient over a guidewire 177, operation of the motor 113 rotates the impeller 143 within the vasculature while the guidewire 177 extends through the guidewire lumen 175. In certain embodiments, the device 101 is operable when the guidewire 177 extends distally out of a distal tip 181 of device 101 (that is, even with the guidewire 177 extending out of the distal tip, the motor 113 can be operated to drive the impeller 143). The over-the-wire impeller embodiments of the device 101 may include a purge system. In such embodiments, when the device 101 is inserted into the vasculature of the patient over the guidewire, the purge fluid 125 continually purges the catheter 107 when the motor 113 is operated and the purge fluid 125 continually purges the catheter 107 when the motor 113 is not operated. Preferably, when the impeller 143 is inserted into vasculature of a patient, the purge fluid 125 purges the catheter 107 by hydrostatic pressure while the motor 113 is not operated and the purge fluid 125 purges the catheter by centrifugal force while the motor 113 is operated.

Thus the disclosure provides a device 101 having an impeller 143 disposed at a distal portion 108 of a catheter 107 and dimensioned for insertion into vasculature of a patient, wherein when the impeller 143 is inserted into the vasculature of a patient, a purge fluid 125 purges the catheter 107 by hydrostatic pressure while the impeller 143 is not being rotated and the purge fluid 125 purges the catheter 107 by centrifugal force while the impeller 143 is being rotated.

Additionally, the disclosure provides a device 101 with an impeller 143 dimensioned for insertion into vasculature of a patient, a guidewire lumen 175 extending through the impeller 143, and a drive mechanism 130 operable to rotate the impeller 143 while the impeller 143 is in the vasculature with a guidewire 177 extending through the guidewire lumen 175. The drive mechanism 130 may include a hollow driveshaft 111 extending proximally from the impeller 143 to a motor 113. The hollow driveshaft 111 preferably extends through a catheter 107 having a proximal portion 106 and a distal portion 108, in which the impeller 143 is distal to the distal portion 108 and the motor 113 is proximal to the proximal portion 106 (see, e.g., FIG. 2). In some embodiments, the motor 113 sits in a housing 105 connected to the proximal portion 106 of the catheter 107. The motor 113 may include a stator 131 housed within the housing 105 and a rotor 127 disposed within the stator 131, with the guidewire lumen 175 extending through the impeller 143, through the driveshaft 111, and through the rotor 127. Optionally, the guidewire lumen 175 opens to a tapered port 115 at a proximal portion 104 of the housing 105. The device 101 may include a hollow atraumatic tip 180 extending distally from the impeller 143. The hollow driveshaft 111 may extend through an extended catheter 107, with the impeller 143 disposed at a distal portion 108 of the catheter 107 and preferably with the motor 113 disposed at a proximal portion 106 of the catheter 107.

Figure 6:
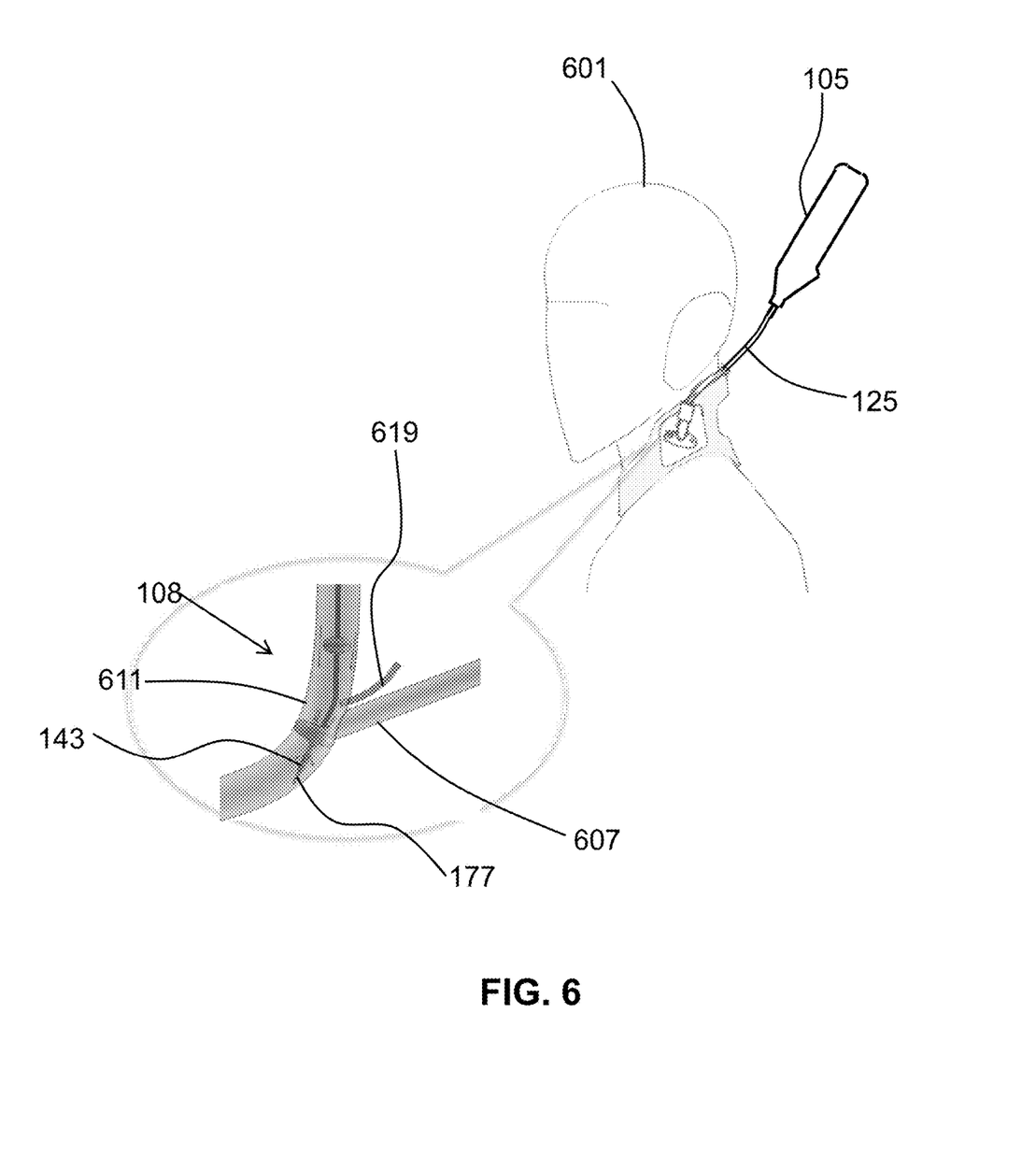
FIG. 6 illustrates a device in use for treatment of a patient.

FIG. 6 illustrates a device 101 in use for treatment of a patient 601. The device 101 has been inserted into vasculature of the patient 601 such that the housing 105 sits outside the patient 601 and the distal portion 108 of the catheter sits in the left jugular vein 611 near the junction with the left subclavian vein 607, thereby servicing an outflow of the thoracic duct 619. The impeller sits over the guidewire 177 and can operate (rotate) while sitting over the guidewire 177. The purge fluid 125 is provided through the catheter and washes the impeller 143 and prevents bodily fluid from entering the device 101.

Figure 7:
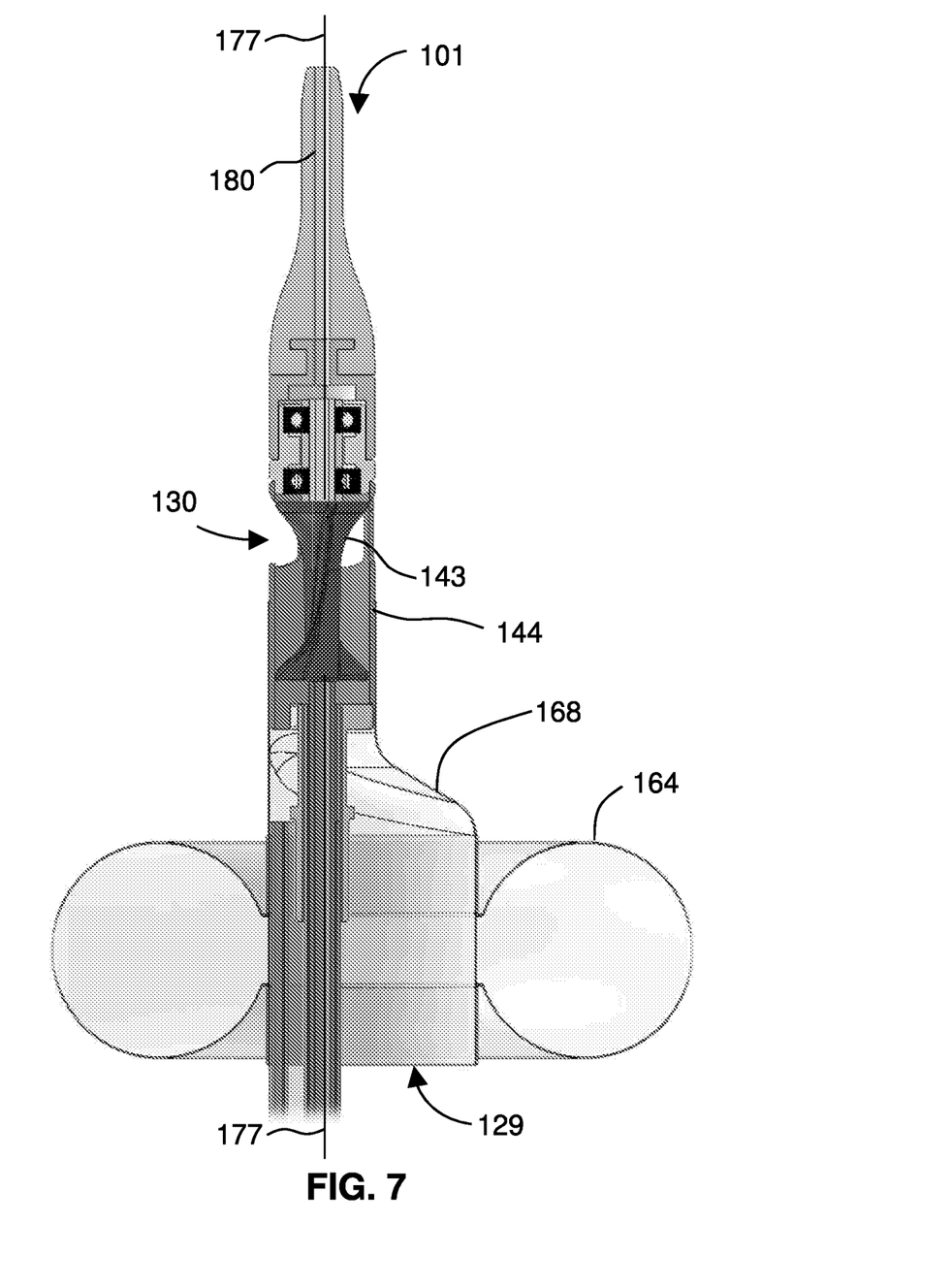
FIG. 7 gives a detail view of the distal portion and distal tip of the catheter.

FIG. 7 gives a detail view of the distal portion 108 and distal tip 180 of the catheter 107 on the device 101. The impeller 143 sits in the impeller housing 144, preferably just downstream of an expandable membrane 168, which is connected to an inflatable balloon 164. When the balloon 164 is inflated, it forms a torus surrounding the catheter 107 and it forms the expandable membrane 168 into a tapered conduit. A proximal end of the expandable membrane 168, ringed by the toroidal balloon 164, forms an inlet port 129 to the conduit, and the conduit continues into the impeller housing 144 to one or more outlet ports 130, which may be disposed along one or more sides of the housing 144. A guidewire 177 may be extended through the device, through the guidewire lumen 175. The impeller 143 is connected to a drive mechanism 130 (not pictured) through a hollow drive shaft 111. A hollow, atraumatic tip 180 sits distal to the impeller and completes the guidewire lumen 175. The guidewire 177 extends from the tip 180. The impeller housing 144 is connected to the distal portion 108 of the catheter 107. As shown, the device 101 includes at least one inlet port 129 proximal to the impeller 143 and at least one outlet port 130 distal to the impeller 143, such that rotation of the impeller 143 impels liquid through the impeller housing 144. For the at least one expandable member 163 (e.g., the balloon 164) on the distal portion 108 of the catheter 107, at least one inflation lumen 160 extends through the catheter 107. As shown, the expandable member 163 may include a substantially toroidal balloon 164 connected to the catheter 107 or impeller housing 144 by an expandable membrane 168. When the catheter 107 is inserted over a guidewire 177 into the vasculature, the balloon 164 can be inflated and the impeller 143 the can be rotated by operation of the motor 113 while the guidewire 177 extends through the device 101.

Figure 8:
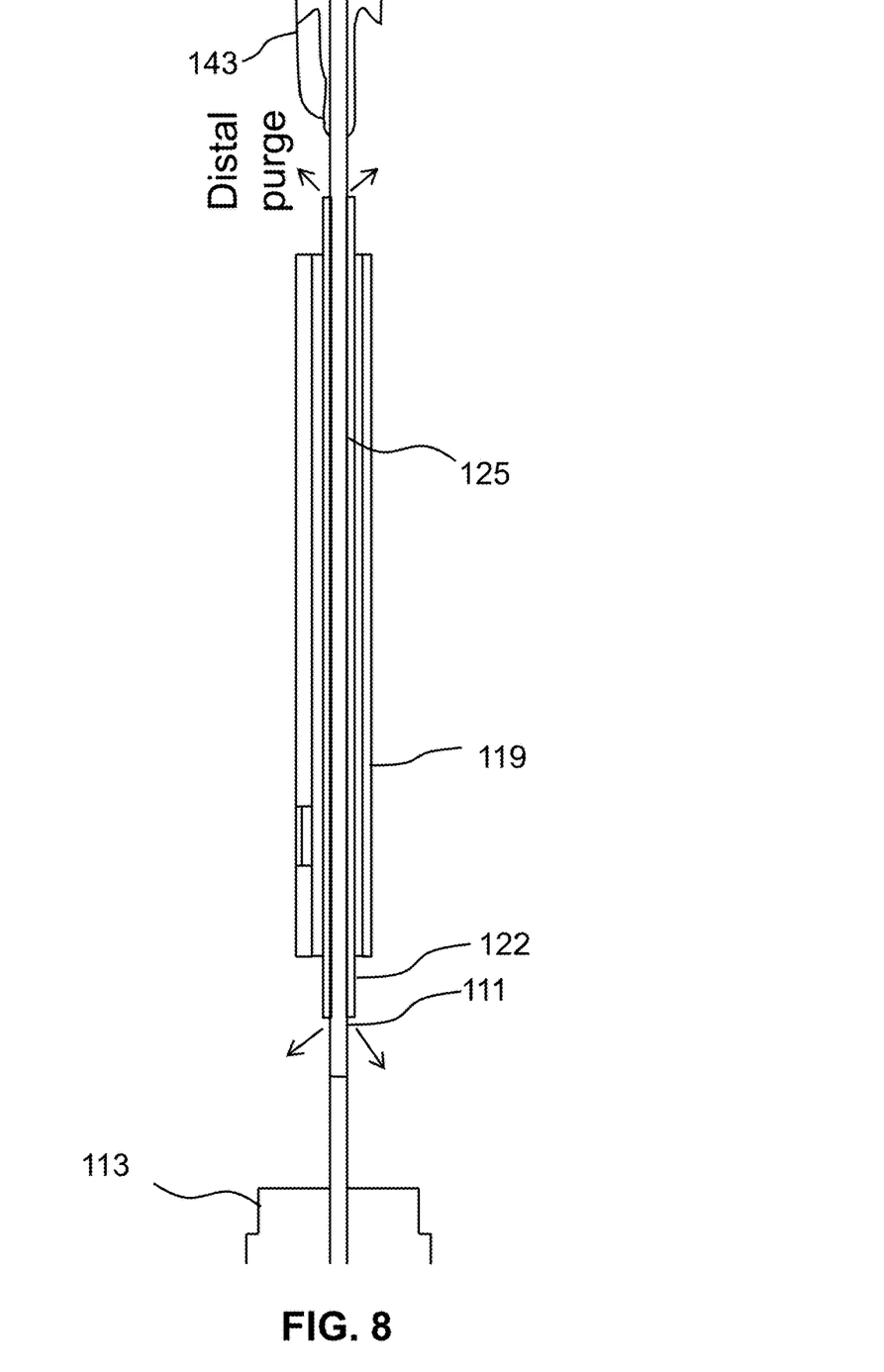
FIG. 8 is a cross-sectional view through a tube portion of the device.

FIG. 8 is a cross-sectional view through the tube 119, showing the drive shaft 111 extending from the motor 143 to the impeller 143. The tube 119 surrounds a sleeve 122 which sits around the drive shaft 111. The purge fluid 125 arrives through the porous drive shaft 111 and is under either or both of hydrostatic pressure and centrifugal force to prevent blood from entering the catheter.

Figure 9:
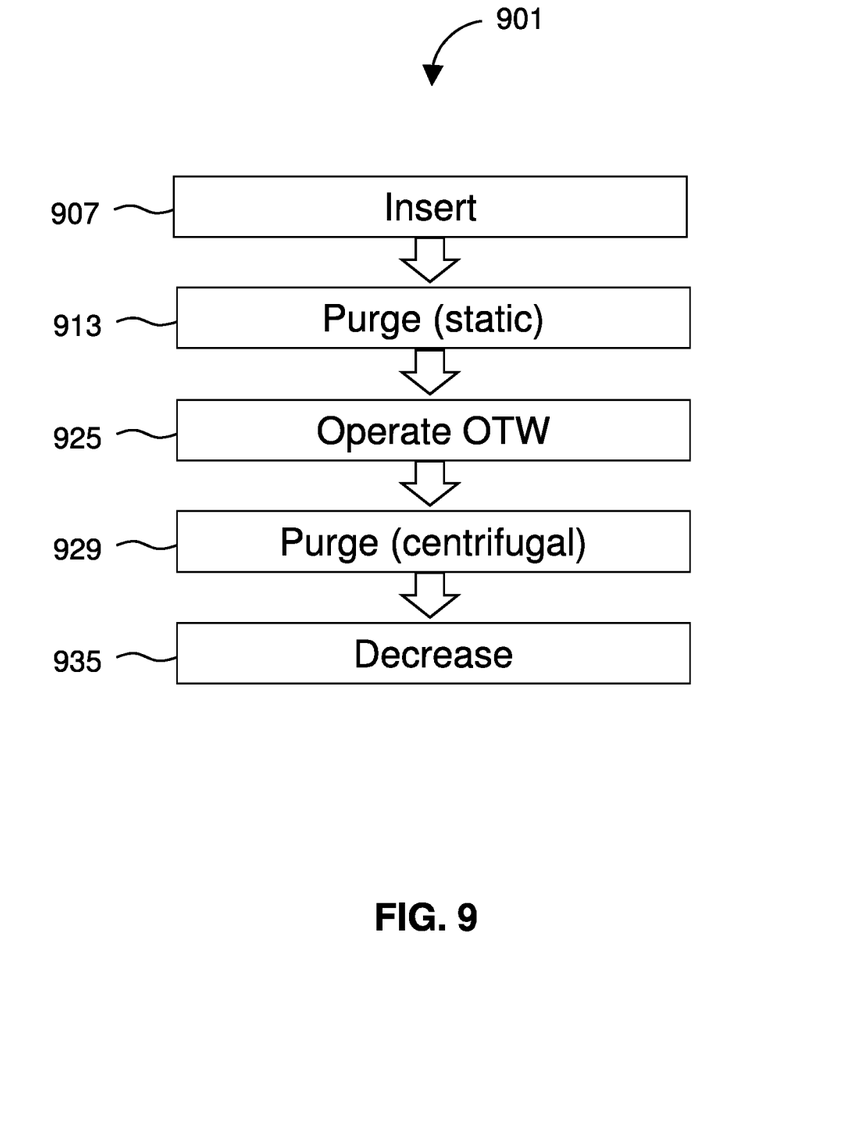
FIG. 9 diagrams a method of treating a patient using a device of the disclosure.

FIG. 9 diagrams a method 901 of treating a patient that may be performed using a device 101 of the disclosure. The method 901 includes inserting 907 a distal portion 108 of the catheter 107 into vasculature of a patient (over a guidewire 177) and navigating the distal portion 108 to a treatment site, such as an outlet of a thoracic duct 619. The method 901 may include purging 913 the catheter 107 by hydrostatic pressure of the purge fluid 125 while the device sits in the vasculature (e.g., within the jugular vein 611). The device may be operated 925 while over the wire. For example, the impeller 143 may be rotated by driving the motor 113, even while the guide wire 177 extends through the impeller shaft lumen. While the device is operated 925, the device 101 is purged 929 by centrifugal force and other forces of fluid dynamics. The purging 913, 929 by the purge fluid 125 allows the impeller 143 to operate 925 reliably, and the positioning over-the-wire (OTW) places the distal portion 108 in the correct location proximal to an outflow of a thoracic duct 619. By such means, the device 101 decreases 935 pressure at the thoracic duct 619, thereby relieving edema and aiding in the treatment of congestive heart failure.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification, and guidance that can be adapted to the practice of this invention in its various embodiments and equivalents thereof.

What is claimed is:

1. A device comprising:
a catheter dimensioned for insertion into a bodily lumen;
a motor housing disposed at a proximal portion of the catheter;
a motor housed within the motor housing;
an impeller housing coupled to a distal portion of the catheter, wherein the impeller housing comprises an impeller disposed therein, the impeller comprising an impeller shaft and one or more blades disposed along the impeller shaft, at least one inlet port proximal to the impeller, and at least one outlet port distal to the impeller such that rotation of the impeller impels fluid through the impeller housing from the at least one inlet port to the at least one outlet port;
an inflatable balloon coupled to the impeller housing;
a drive shaft extending from the motor through the catheter and connected to the impeller shaft;
a tube having at least a portion of the drive shaft housed therein; and
an infusion channel in fluid communication with the drive shaft and arranged such that purge fluid is delivered and discharged from the infusion channel through a gap between the impeller and the tube to prevent bodily fluid from entering the tube, wherein when the impeller is disposed within vasculature of a patient the infusion channel is configured to deliver the purge fluid such that, when the motor is operated to rotate the impeller to pump blood through the impeller housing, the purge fluid is discharged through the gap to rinses at least a portion of the impeller and, when the motor is not operating and the impeller is not rotating, the purge fluid is discharged through the gap to purge the catheter via a hydrostatic pressure.

2. The device of claim 1, wherein the motor comprises a rotor disposed within a stator in the motor housing at a proximal portion of the catheter.

3. The device of claim 2, wherein the drive shaft is coupled to, and extends from, the rotor.

4. The device of claim 3, wherein a proximal end of the tube includes a proximal sealed connection around the drive shaft, and further wherein operation of the motor rotates the drive shaft within the tube.

5. The device of claim 4, wherein a distal end of the tube includes a distal sealed connection around the drive shaft.

6. The device of claim 5, wherein when the impeller is inserted into vasculature of a patient, the proximal sealed connection, the tube, and/or the distal sealed connection separate the purge fluid within the drive shaft from blood within the catheter outside of the tube.

7. The device of claim 2, wherein the impeller shaft has an impeller shaft lumen therethrough and one or more holes along a side of the impeller shaft such that rotation of the impeller in a liquid subjects the liquid to centrifugal force at the one or more holes.

8. The device of claim 1, wherein the impeller and the drive shaft define a guidewire lumen that extends through the impeller and the drive shaft.

9. The device of claim 8, wherein the guidewire lumen extends through the motor, further wherein when the device is inserted into vasculature of a patient over a guidewire, operation of the motor rotates the impeller within the vasculature while the guidewire extends through the guidewire lumen.

10. The device of claim 9, wherein the device is operable when the guidewire extends distally out of a distal tip of device.

11. The device of claim 9, wherein when the device is inserted into the vasculature of the patient over the guidewire:
the purge fluid continually purges the catheter when the motor is operated; and
the purge fluid continually purges the catheter when the motor is not operated.

12. The device of claim 1, wherein when the motor is rotating, the purge fluid is subject to centrifugal force along the drive shaft preventing the bodily fluid from approaching the proximal portion of the catheter.

13. The device of claim 1, wherein the balloon is in fluid communication with an inflation lumen extending along the catheter.

14. The device of claim 1, wherein when the impeller is inserted into vasculature of a patient, the purge fluid purges the catheter by hydrostatic pressure while the motor is not operated and the purge fluid purges the catheter by centrifugal force while the motor is operated.

15. The device of claim 1, wherein the inflatable balloon, when inflated, forms a torus surrounding the impeller housing.

16. The device of claim 1, wherein the impeller is seated within the impeller housing by at least one support ring, wherein the support ring comprises an open central ring supported within an outer ring by multiple spokes.

* * * * *